_(12)_ United States Patent
Takata

(10) Patent No.: US 8,560,061 B2
(45) Date of Patent: Oct. 15, 2013

(54) NERVE STIMULATION APPARATUS, NERVE STIMULATION SYSTEM, AND CONTROL METHOD FOR NERVE STIMULATION APPARATUS

(75) Inventor: Yuhei Takata, Tokyo (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 13/418,712

(22) Filed: Mar. 13, 2012

(65) Prior Publication Data

US 2013/0013015 A1 Jan. 10, 2013

(30) Foreign Application Priority Data

Jul. 8, 2011 (JP) ................. 2011-151710

(51) Int. Cl.
*A61N 1/00* (2006.01)
(52) U.S. Cl.
USPC ............................................................ 607/2
(58) Field of Classification Search
USPC .............................................. 607/18, 59, 62
See application file for complete search history.

(56) References Cited

U.S. PATENT DOCUMENTS

2010/0063564 A1* 3/2010 Libbus et al. ................... 607/62
2012/0095530 A1* 4/2012 Chavan et al. .................. 607/59
2012/0310295 A1* 12/2012 Libbus et al. ................... 607/18

FOREIGN PATENT DOCUMENTS

| JP | 2008-534218 | 8/2008 |
| JP | 2009-531156 | 9/2009 |
| WO | WO 2006/107675 A1 | 10/2006 |
| WO | WO 2007/115113 A1 | 10/2007 |

OTHER PUBLICATIONS

English Abstract of International Publication No. WO 2006/107675 A1, dated Oct. 12, 2006.
English Abstract of International Publication No. WO 2007/115113 A1, dated Oct. 11, 2007.
Li, Meihua et al., "Vagal Nerve Stimulation Markedly Improves Long-Term Survival After Chronic Heart Failure in Rats", Circulation (2004), vol. 109, No. 1, pp. 120-124.

* cited by examiner

*Primary Examiner* — Robert N Wieland
(74) *Attorney, Agent, or Firm* — Scully, Scott, Murphy & Presser, P.C.

(57) ABSTRACT

A sufficient therapeutic effect is achieved for each of a plurality of pathologies constituting a cardiac failure. Provided is a nerve stimulation apparatus including: a heartbeat detection unit that detects a heartbeat; a nerve electrode that is connected to a nerve controlling a heart; a nerve stimulation unit that outputs an electrical pulse to the nerve electrode; a functional-status detection unit that detects in-vivo information that indicates a functional status of the heart; and a stimulation-timing controller that controls the nerve stimulation unit so as to switch between a synchronous mode in which the electrical pulse is output in synchronization with the heartbeat detected by the heartbeat detection unit and an asynchronous mode in which the electrical pulses are output at constant time intervals, on the basis of the in-vivo information that indicates the functional status of the heart detected by the functional-status detection unit.

9 Claims, 10 Drawing Sheets

FIG. 4

| | | | |
|---|---|---|---|
| HEART RATE | R≧R1 | SECOND STIMULATION MODE (LOW-FREQUENCY/ SYNCHRONIZATION WITH HEARTBEAT) | FIRST STIMULATION MODE (HIGH-FREQUENCY/ SYNCHRONIZATION WITH HEARTBEAT) |
| | R<R1 | FOURTH STIMULATION MODE (LOW-FREQUENCY/ HEARTBEAT ASYNCHRONIZATION) | THIRD STIMULATION MODE (HIGH-FREQUENCY/ HEARTBEAT ASYNCHRONIZATION) |
| | | L<L1 | L≧L1 |
| | | CARDIAC DILATATION LEVEL | |

NERVE STIMULATION APPARATUS, NERVE STIMULATION SYSTEM, AND CONTROL METHOD FOR NERVE STIMULATION APPARATUS

BACKGROUND OF THE INVENTION

1. Field of the Invention

The present invention relates to a nerve stimulation apparatus, a nerve stimulation system, and a control method for a nerve stimulation apparatus.

This application is based on Japanese Patent Application No. 2011-151710, the content of which is incorporated herein by reference.

2. Description of Related Art

In the related art, stimulation of the vagus nerve is known to have an effect of reducing the heart rate. An apparatus that uses this effect to treat cardiac failure by stimulating the vagus nerve in synchronization with the heartbeat is known (for example, see PCT International Publication No. WO2007/115113 and PCT International Publication No. WO2006/107675).

On the other hand, it is known that disorder of pumping function and remodeling of the heart can be prevented by stimulating the vagus nerve following cardiac infarction (for example, see Meihua Li, et al., "Vagal Nerve Stimulation Markedly Improves Long-Term Survival After Chronic Heart Failure in Rats", Circulation, Vol. 109, No. 1, pp. 120-124).

In treatment for preventing cardiac remodeling following cardiac infarction, the frequency of electrical stimulation supplied to the vagus nerve is important. On the other hand, in treatment of tachycardia and fibrillation, the timing of electrical stimulation applied to the vagus nerve is important.

BRIEF SUMMARY OF THE INVENTION

A first aspect of the present invention is a nerve stimulation apparatus including a heartbeat detection unit that detects a heartbeat; a nerve electrode that is connected to a nerve controlling a heart; a nerve stimulation unit that outputs an electrical pulse to the nerve electrode; a functional-status detection unit that detects in-vivo information that indicates a functional status of the heart; and a stimulation-timing controller that controls the nerve stimulation unit so as to switch between a synchronous mode in which the electrical pulse is output in synchronization with the heartbeat detected by the heartbeat detection unit and an asynchronous mode in which the electrical pulses are output at constant time intervals, on the basis of the in-vivo information that indicates the functional status of the heart detected by the functional-status detection unit.

A second aspect of the present invention is a nerve stimulation system including a nerve stimulation apparatus described above that is indwelled in body; and an external apparatus that is arranged outside body and that detects in-vivo information that indicates the organ status or the organ status of the heart; wherein the nerve stimulation apparatus is equipped with an in-vivo information acquisition unit that acquires in-vivo information detected by the external apparatus; and a stimulation-frequency controller that controls the nerve stimulation unit so as to switch between a high-frequency mode in which the electrical pulses are output at a relatively high frequency and a low-frequency mode in which the electrical pulses are output at a relatively low frequency, on the basis of the in-vivo information acquired by the in-vivo information acquisition unit.

A third aspect of the present invention is a control method for a nerve stimulation apparatus for controlling a setting of an electrical pulse output from a pulse generator to an electrode with a controller provided to a nerve stimulation apparatus, wherein the controller controls the pulse generator so as to switch between a synchronous mode in which the electrical pulses are output in synchronization with a heartbeat and a asynchronous mode in which the electrical pulses are output at constant time intervals, on the basis of in-vivo information that indicates the functional status of the heart detected by a functional-status detection unit.

BRIEF DESCRIPTION OF THE SEVERAL VIEWS OF THE DRAWINGS

FIG. 4 is a table showing relationships between the heart rate, the cardiac dilatation level, and the stimulation mode in a pulse-setting selection unit in FIG. 2.

DETAILED DESCRIPTION OF THE INVENTION

A nerve stimulation apparatus 1 according to an embodiment of the present invention will be described below, with reference to the drawings.

Figure 1:
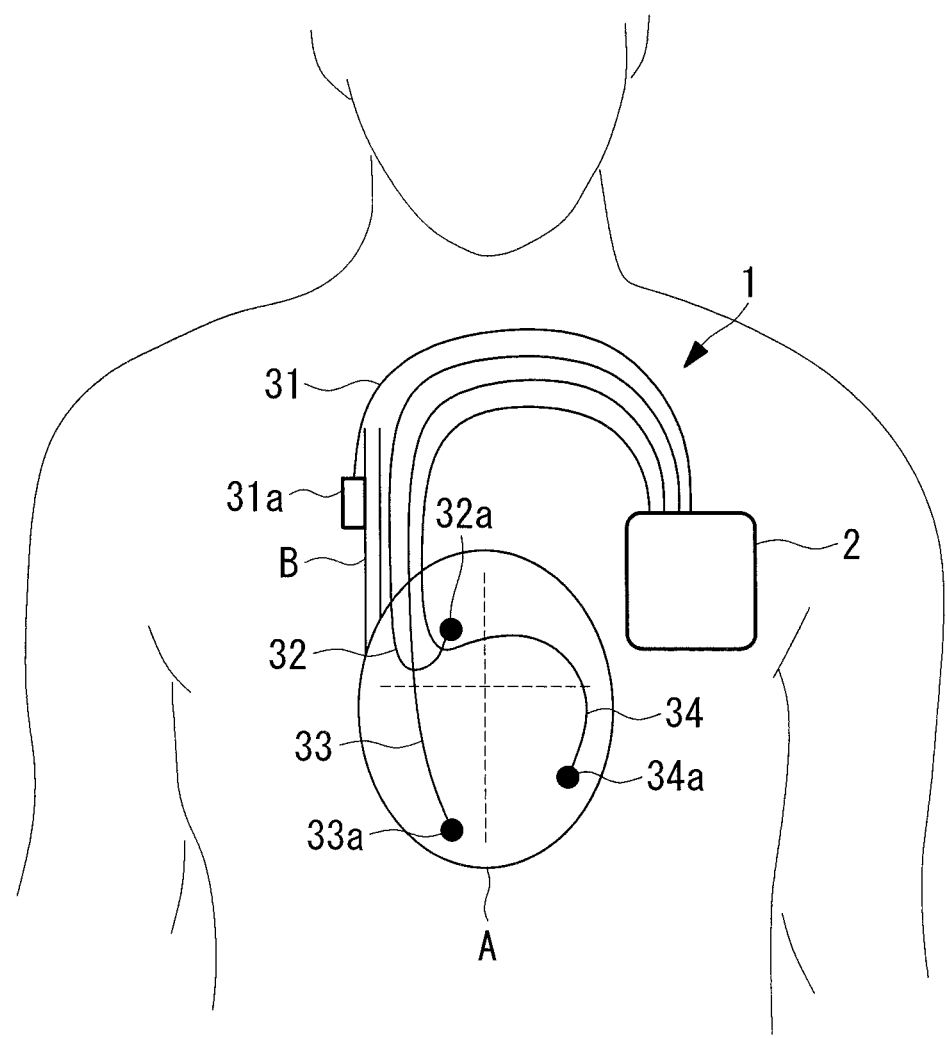
FIG. 1 is a diagram showing, in outline, the configuration of a nerve stimulation apparatus according to an embodiment of the present invention.

As shown in FIG. 1, the nerve stimulation apparatus 1 according to this embodiment is equipped with an implanted main unit 2 and four leads 31, 32, 33, and 34 extending from the main unit 2.

Tips of the four leads 31, 32, 33, and 34 are provided with a nerve electrode 31a, an RA (right atrium) electrode 32a, an RV (right ventricle) electrode 33a, and an LV (left ventricle) electrode 34a, respectively. The nerve electrode 31a is connected to the vagus nerve (nerve) B, which is the parasympathetic nerve controlling the heart A and is found near the heart A. The RA electrode 32a, the RV electrode 33a, and the LV electrode 34a are connected to the right atrium, the right ventricle, and the left ventricle, respectively. Each of these electrodes 31a, 32a, 33a, and 34a is formed of a ring electrode and a tip electrode.

Figure 2:
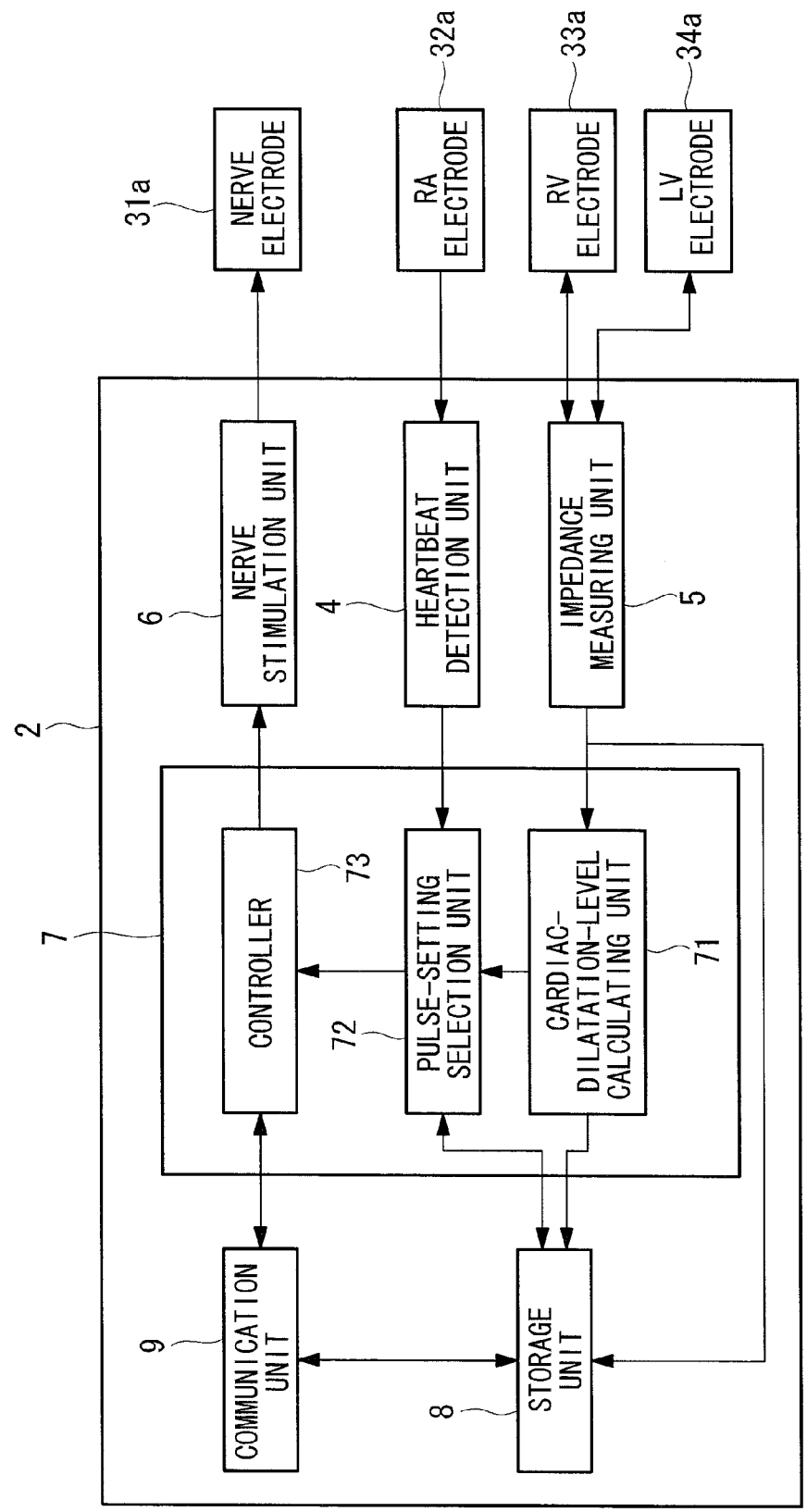
FIG. 2 is a block diagram showing the internal configuration of a main unit of the nerve stimulation apparatus of FIG. 1.

As shown in FIG. 2, the main unit 2 is provided with a heartbeat detection unit (functional-status detection unit) 4 that detect the heartbeat, an impedance measuring unit (organ-status detection unit) 5 that measures a left ventricular impedance (in-vivo information), a nerve stimulation unit 6 that supplies a stimulation pulse (electrical pulse) to the vagus nerve B, a CPU (central processing unit) 7 that processes signals from the heartbeat detection unit 4 and the impedance measuring unit 5 and outputs an instruction signal for operating the nerve stimulation unit 6, a storage unit 8, and a communication unit 9.

The heartbeat detection unit 4 detects the electrocardiac signal with at least one of the three electrodes 32a, 33a, and 34a connected to the heart A (in the illustrated example, the RA electrode 32a), determines the appearance of the R wave in the electrocardiac signal, and detects the heartbeat when, for example, the electric potential of the electrocardiac signal exceeds a predetermined threshold on the basis of a change in the waveform of the detected electrocardiac signal. As the heartbeat is detected, the heartbeat detection unit 4 outputs a heartbeat detection signal to a pulse-setting selection unit 72 (described below) in the CPU 7.

Figure 3:
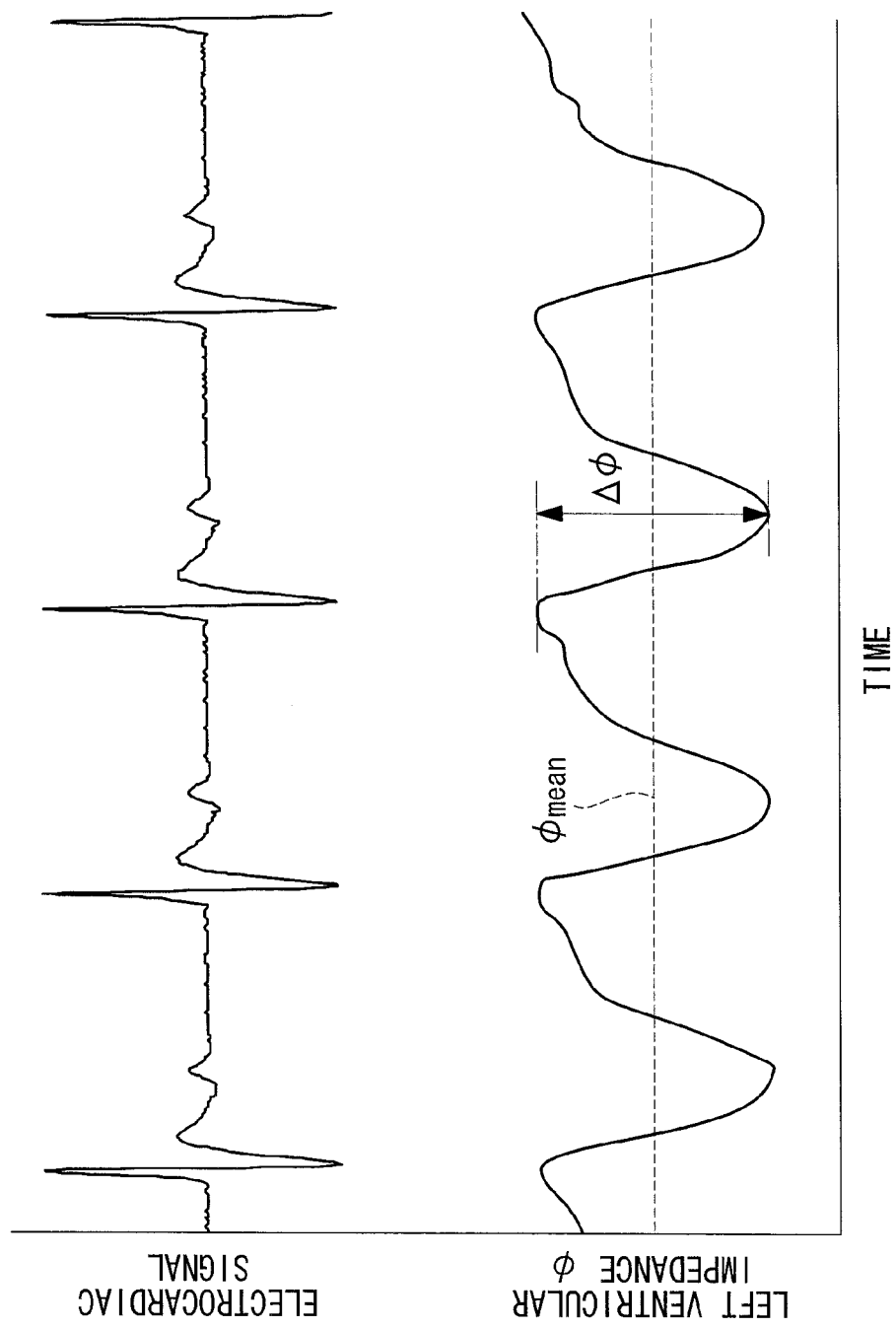
FIG. 3 is a diagram showing a time-relationship between an electrocardiac signal detected by a heartbeat detection unit in FIG. 2 and the left ventricular impedance measured by an impedance measuring unit.

The impedance measuring unit 5 applies a voltage across the RV electrode 33a and the LV electrode 34a and measures the magnitude of the voltage drop thereof, thereby measuring the left ventricular impedance $\Phi$ of the left ventricle region located between the two electrodes 33a and 34a. As shown in FIG. 3, the left ventricular impedance $\Phi$ is in-vivo information that varies in synchronization with the heartbeat and, as described below, is an indicator of cardiac dilatation, which is an abnormal organ status of the heart. The impedance measuring unit 5 repeatedly determines the left ventricular impedance $\Phi$ at sufficiently shorter time intervals than the heartbeat and successively stores them in the storage unit 8.

The nerve stimulation unit 6 generates the stimulation pulse and outputs the generated stimulation pulse to the nerve electrode 31a. The stimulation pulse is supplied to the vagus nerve B via the nerve electrode 31a.

The CPU 7 is provided with a cardiac-dilatation-level calculating unit 71 that calculates a cardiac dilatation level L on the basis of the left ventricular impedance $\Phi$ measured by the impedance measuring unit 5, the pulse-setting selection unit 72 that selects one of the four stimulation modes on the basis of information from the heartbeat detection unit 4 and the cardiac-dilatation-level calculating unit 71, and a controller (stimulation-timing controller and stimulation-frequency controller) 73 that causes the stimulation pulse to be output from the nerve stimulation unit 6 in the stimulation mode selected by the pulse-setting selection unit 72.

The cardiac-dilatation-level calculating unit 71 calculates an average value $\Phi$mean and a variation range $\Delta\Phi$ of the left ventricular impedance $\Phi$ for every heartbeat and also calculates the cardiac dilatation level L that indicates the organ status of the heart A from these values, $\Phi$mean and $\Delta\Phi$. Specifically, when the heartbeat detection signal is input to the cardiac-dilatation-level calculating unit 71 from the heartbeat detection unit 4, the cardiac-dilatation-level calculating unit 71 reads out the left ventricular impedance $\Phi$ stored in the storage unit 8 up to this point. The cardiac-dilatation-level calculating unit 71 then calculates the average value $\Phi$mean of the read out left ventricular impedance $\Phi$ and, in addition, calculates the variation range $\Delta\Phi$, which is a difference between the maximum value and the minimum value of left ventricular impedance $\Phi$, from the left ventricular impedance $\Phi$ for a preceding heartbeat. For example, the cardiac-dilatation-level calculating unit 71 calculates the cardiac dilatation level L in accordance with $L = A*\Phi mean/\Delta\Phi$, wherein A is a constant.

The average value $\Phi$mean is an indicator of the size of the cardiac lumen, and the variation range $\Delta\Phi$ is an indicator of the contractile force of the heart A. In other words, the more severe the cardiac dilatation is, the larger the average value $\Phi$mean and the smaller the variation range $\Delta\Phi$ become, and therefore, the larger the cardiac dilatation level L becomes. On the other hand, the less severe the cardiac dilatation is, the smaller the average value $\Phi$mean and the larger the variation range $\Delta\Phi$ become, and therefore, the smaller the cardiac dilatation level L becomes.

When the heartbeat detection signal is input to the pulse-setting selection unit 72 from the heartbeat detection unit 4, the pulse-setting selection unit 72 calculates the heart rate (in-vivo information) R from intervals between the input times of the heartbeat detection signals, in other words, time intervals of the heartbeat. The pulse-setting selection unit 72 determines which of the first to the fourth stimulation modes corresponds to the combination of the heart rate R and the cardiac dilatation level L calculated in the cardiac-dilatation-level calculating unit 71.

Specifically, as shown in FIG. 4, the pulse-setting selection unit 72 determines the mode as follows and selects the determined stimulation mode:

when $R \geq R1$ and $L \geq L1$, the first stimulation mode (synchronous mode, high-frequency mode);

when $R \geq R1$ and $L < L1$, the second stimulation mode (synchronous mode, low-frequency mode);

when $R < R1$ and $L < L1$, the third stimulation mode (asynchronous mode, high-frequency mode); and when $R < R1$ and $L < L1$, the fourth stimulation mode (asynchronous mode, low-frequency mode).

Here, R1 and L1 are thresholds decided depending on the patient receiving implantation of the nerve stimulation apparatus 1. Specifically, by evaluating the state of the patient's heart in advance, the upper limit for the normal heart rate level is set as R1, and the upper limit for the mild cardiac dilatation level is set as L1. These values R1 and L1 are stored in the storage unit 8.

The controller 73 instructs the nerve stimulation unit 6 so that stimulation pulses having settings corresponding to the stimulation mode selected by the pulse-setting selection unit 72 are generated and output.

Figure 5A:
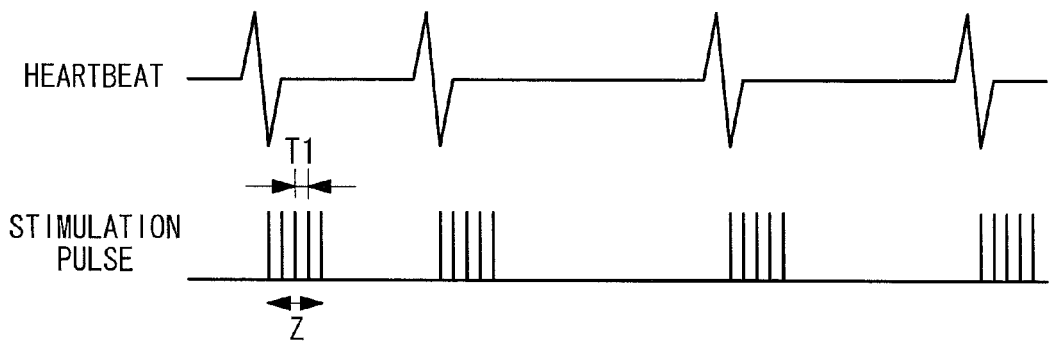
FIG. 5A is a diagram for explaining settings of stimulation pulses output from the nerve stimulation apparatus of FIG. 1 in a first stimulation mode.

As shown in FIG. 5A, the first stimulation mode is a mode in which a plurality of stimulation pulses are output over a duration Z from the time at which the heartbeat is detected by the heartbeat detection unit 4. The duration Z is sufficiently shorter than the time intervals between heartbeats.

Figure 5B:
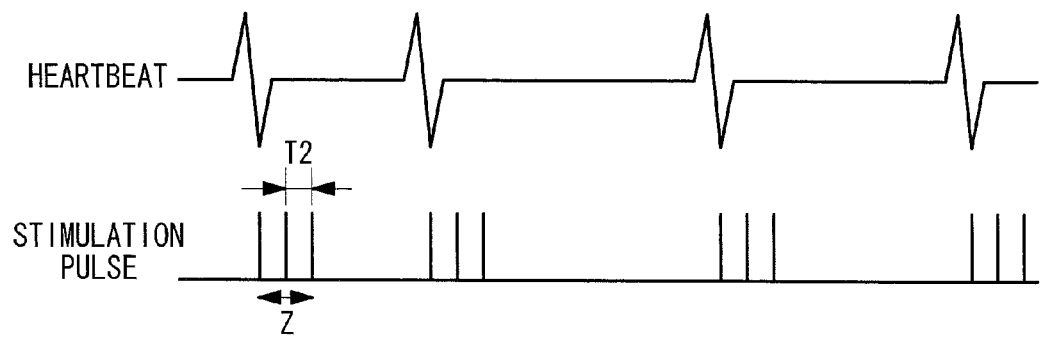
FIG. 5B is a diagram for explaining settings of stimulation pulses output from the nerve stimulation apparatus of FIG. 1 in a second stimulation mode.

As shown in FIG. 5B, in the second stimulation mode, stimulation pulses having a pulse period T2 are output over the duration Z when the heartbeat is detected by the heartbeat detection unit 4. The pulse period T2 is longer than a pulse period T1 of the stimulation pulses in the first stimulation mode. In other words, the second stimulation mode is the mode in which the stimulation pulses are output at lower frequency compared with the first stimulation mode.

Figure 5C:
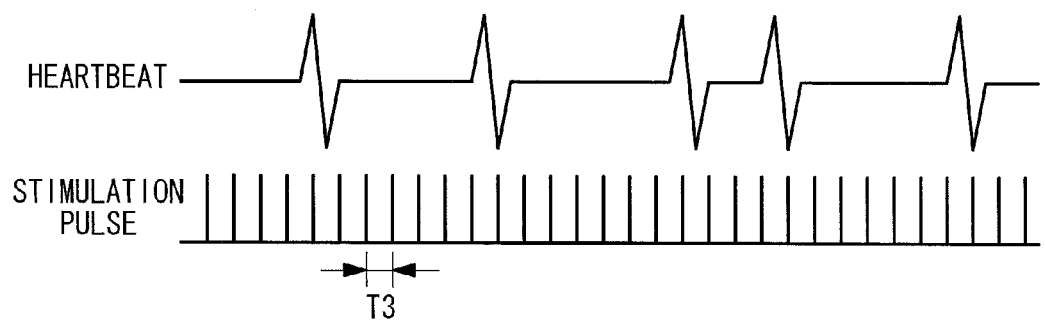
FIG. 5C is a diagram for explaining settings of stimulation pulses output from the nerve stimulation apparatus of FIG. 1 in a third stimulation mode.

As shown in FIG. 5C, the third stimulation mode is a mode in which stimulation pulses are continuously output with a constant pulse period T3 regardless of the heartbeat.

Figure 5D:
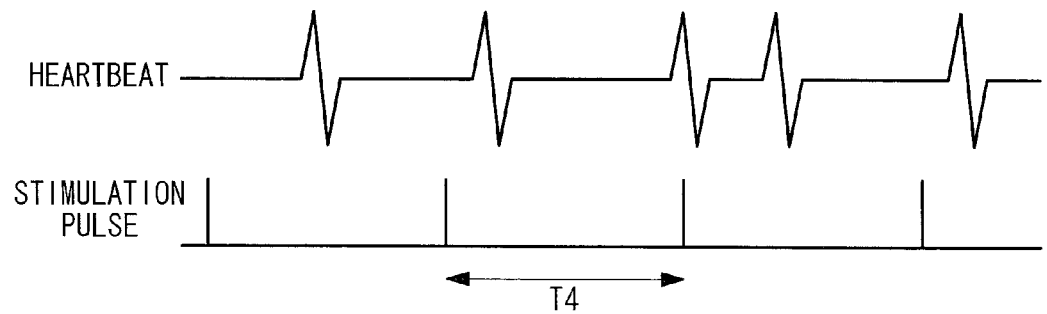
FIG. 5D is a diagram for explaining settings of stimulation pulses output from the nerve stimulation apparatus of FIG. 1 in a fourth stimulation mode.

As shown in FIG. 5D, the fourth stimulation mode is a mode in which stimulation pulses having a pulse period T4 are continuously output regardless of the heartbeat. The fourth pulse period T4 is longer than the pulse period T3 of the stimulation pulses in the third stimulation mode.

The storage unit 8 is formed of a RAM (random-access memory) or a ROM (read-only memory).

The communication unit 9 performs transmission and reception of data with a computer located outside the body through wireless communication. For example, an operator can change the operation settings of the nerve stimulation apparatus 1 by sending signals etc. for changing the settings of the stimulation pulses from the computer to the CPU 7 through the communication unit 9.

Next, the operation of the thus-configured nerve stimulation apparatus 1 will be described.

Figure 6:
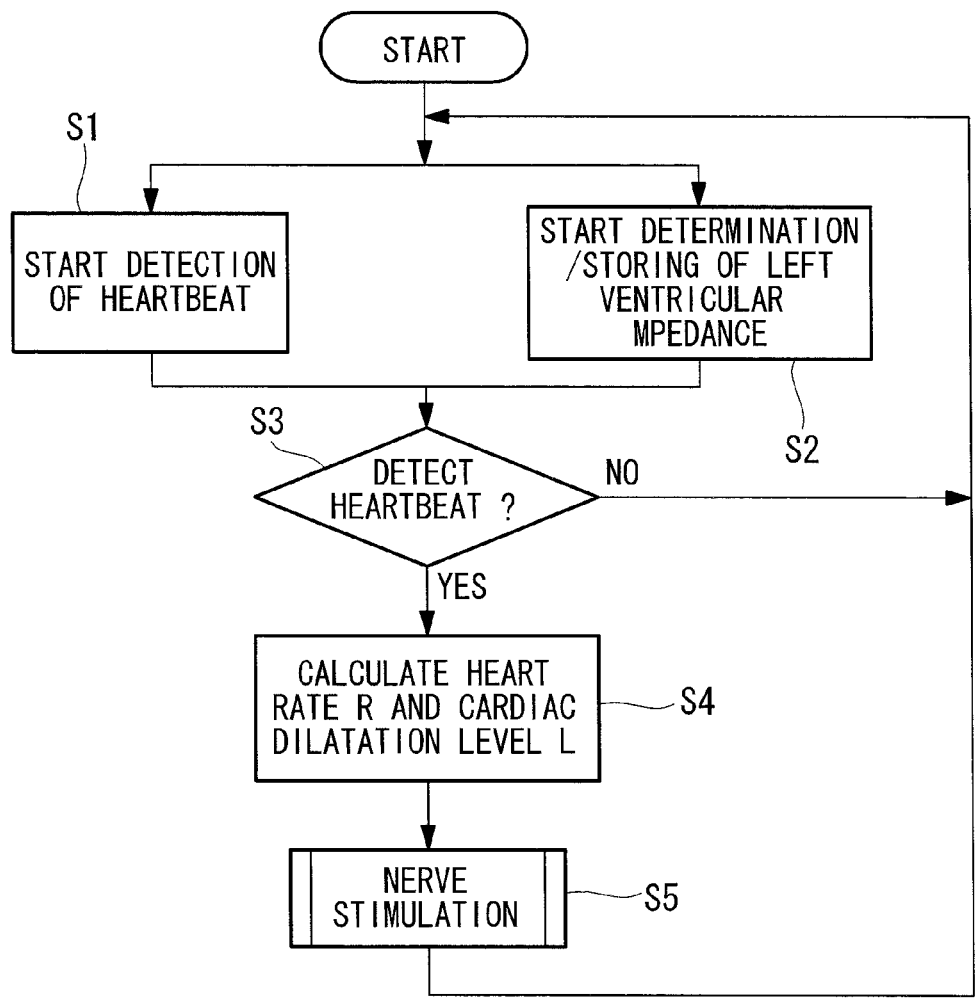
FIG. 6 is a flowchart showing a main routine for operating the nerve stimulation apparatus of FIG. 1.

As shown in FIG. 6, the nerve stimulation apparatus 1 according to this embodiment starts detection of the heartbeat (Step S1), and at the same time, starts measuring and storing the left ventricular impedance Φ (Step S2), and then, the nerve stimulation apparatus 1 calculates the heart rate R and the cardiac dilatation level L for every heartbeat (Step S3, S4). The nerve stimulation apparatus 1 then supplies the stimulation pulses to the vagus nerve B in the stimulation mode selected on the basis of the calculated values R and L (Step S5).

Figure 7:
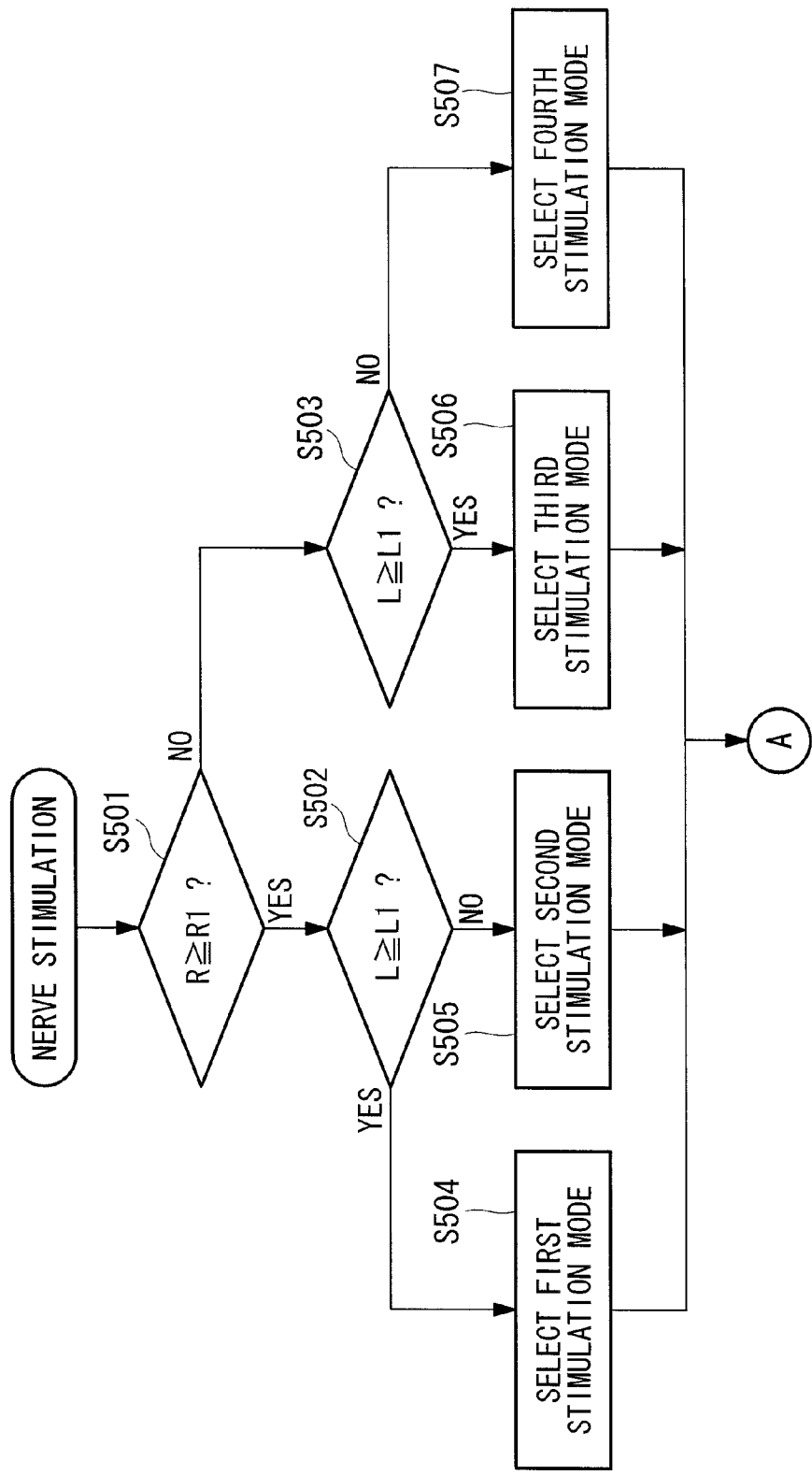
FIG. 7 is a flowchart showing a nerve stimulation routine in the flowchart of FIG. 6.
Figure 8:
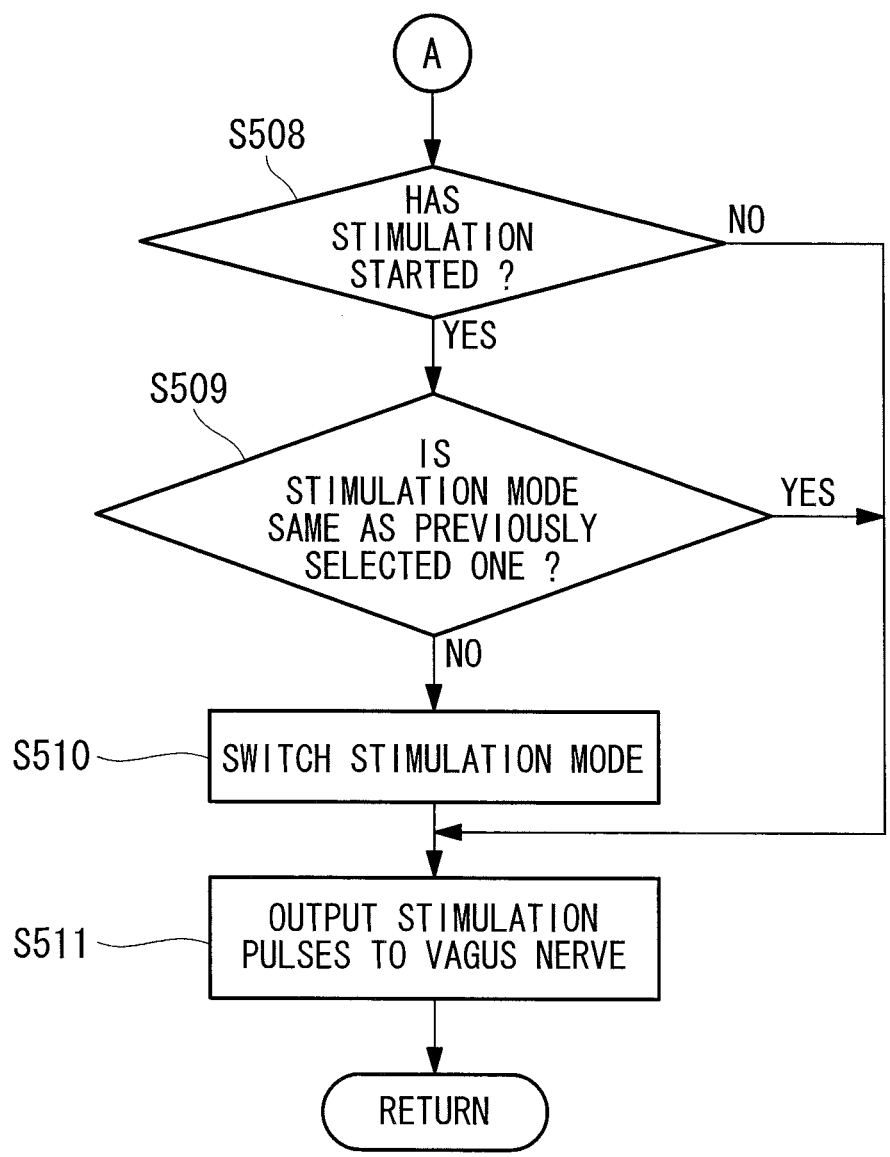
FIG. 8 is a flowchart showing continued steps of the nerve stimulation routine of FIG. 7.

Specifically, as shown in FIGS. 7 and 8, depending on the heart rate R and the cardiac dilatation level L (Steps S501 to S503), the nerve stimulation apparatus 1 selects the stimulation pulse settings from the first to the fourth stimulation modes (Steps S504 to S507). R1 is set as the threshold for determination of tachycardia. In this case, when the heart rate R is higher than R1 (YES at Step S501), the heartbeat is determined to show tachycardia, and so the stimulation is performed in the first or the second stimulation mode (Steps S504 and S505). When the heart rate R is lower than R1 (NO at Step S501), the heartbeat is within a normal range, and so the stimulation is performed in the third or the fourth stimulation mode (Steps S506 and S507). On the other hand, the cardiac dilatation level L gradually changes over a long period of time due to a hypertrophy of the heart A. In other words, the nerve stimulation apparatus 1 performs the stimulation in the second or the fourth stimulation mode during a period of mild cardiac dilatation (NO at Step S502 or NO at Step S503), and when cardiac dilatation has become more severe (YES at Step S502 or YES at Step S503), performs the stimulation by switching the mode to the first or the third stimulation mode (Step S504 or Step S506).

Next, for the initial supply of the stimulation pulses (Step S508), the nerve stimulation apparatus 1 outputs the stimulation pulses in the selected stimulation mode (Step S511). On the other hand, for the second and later supplies of the stimulation pulses (Step S508), the nerve stimulation apparatus 1 determines whether or not the stimulation mode of the preceding stimulation pulse output and the newly selected stimulation mode are the same (Step S509). As a result of the determination, if the modes are the same, the output of the stimulation pulses is continued in the same mode as the preceding stimulation mode (Step S511), and if the modes are different, the mode is changed to the newly selected stimulation mode (S510) to output the stimulation pulses (Step S511).

As described above, according to this embodiment, the synchronicity and asynchronicity of the stimulation pulses with respect to the heartbeat, as well as the frequency, is changed depending on the heart rate R and the cardiac dilatation level L. Cardiac failure is a combined state of a dysfunction of the heart A, such as increased heart rate, and an organ abnormality, such as cardiac dilatation. In other words, according to this embodiment, the stimulation pulses are supplied to the vagus nerve B with a suitably setting corresponding to each of a plurality of pathologies constituting cardiac failure; therefore, it is possible to achieve a sufficient therapeutic effect for the respective pathologies.

Specifically, for increased heart rate R, which corresponds to a dysfunction of the heart A, it is possible to effectively achieve a suppression effect on the heart rate by causing the stimulation timing of the vagus nerve B to be in synchronization with the heartbeat. On the other hand, for progressive cardiac dilatation, which corresponds to an organ abnormality of the heart A, it is possible to effectively achieve an inhibitory effect on the remodeling of the heart A by increasing the frequency of the stimulation of the vagus nerve B regardless of the timing of the heartbeat.

In this embodiment, the heart rate is detected as the in-vivo information that is an indicator of the functional status of the heart A; instead of this, however, the blood pressure, the blood flow rate, or the left ventricular impedance may be detected as the indicator. Thus in-vivo information can be an indicator of the blood pressure, the blood flow rate, or the cardiac output or stroke volume, which are functional statuses of the heart A. By doing so, it is possible to treat the blood pressure, the blood flow rate, the cardiac output, or the stroke volume. The blood pressure can be detected by a blood pressure sensor (not shown). The blood flow rate can be detected by a blood flow rate sensor (not shown).

In addition, when the cardiac output is detected as the functional status of the heart A, a Swan-Ganz catheter located outside the body may be provided instead of the functional-status detection unit illustrated by the heartbeat detection unit 4. In this case, the information related to the cardiac output detected by the Swan-Ganz catheter is sent to the pulse-setting selection unit 72 through the communication unit 9.

In addition, in this embodiment, the left ventricular impedance is detected as the in-vivo information, which is an indicator of the organ status of the heart A, and the cardiac dilatation level calculated therefrom is utilized; instead of this, however, the pulmonary impedance, the cardiac contractile stress, ST elevation in electrocardiac signals, QRS duration in electrocardiac signals, or a level of dyssynchrony between both of the ventricles may be detected.

The pulmonary impedance, the cardiac contractile stress, the ST elevation in electrocardiac signals, the QRS duration in electrocardiac signals and the level of dyssynchrony between both of the ventricles are indicators of pulmonary congestion, cardiac contractile dysfunction, cardiac infarction, and ventricular dyssynchrony, respectively. By doing so, it is possible to treat organ abnormalities, such as pulmonary congestion, cardiac contractile dysfunction, cardiac infarction, and ventricular dyssynchrony.

The pulmonary impedance is measured with the RV electrode 33a and the LV electrode 34a. The cardiac contractile stress is determined by a stress sensor (not shown) located on the heart A. The ST elevation and the QRS duration in electrocardiac signals or the time shift in contraction timing are detected by using the electrocardiac signal detected by the heartbeat detection unit 4.

Figure 9:
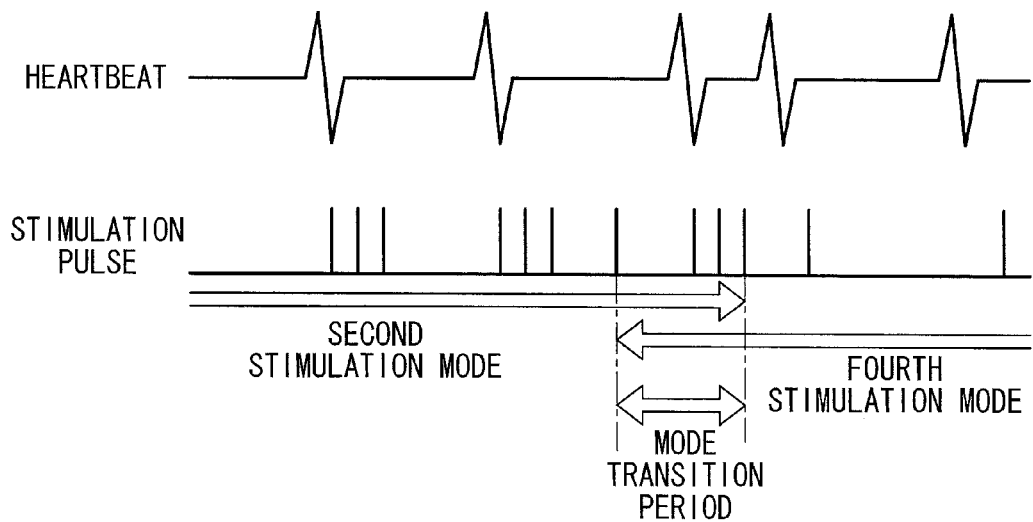
FIG. 9 is a diagram for explaining an example of settings of stimulation pulses during a mode transition period.
Figure 10:
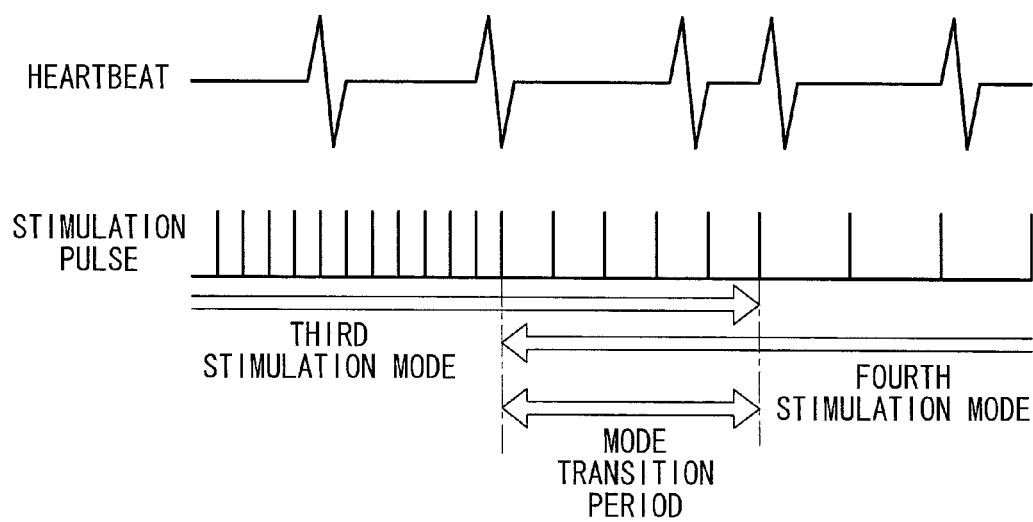
FIG. 10 is a diagram for explaining another example of settings of stimulation pulses during a mode transition period.

In addition, in this embodiment, when the mode is switched from the first or second stimulation mode to the third or fourth stimulation mode, the controller 73 may have a mode transition period during which both stimulation modes before and after the switching are simultaneously performed. For example, when the mode is switched from the second stimulation mode to the fourth stimulation mode, as shown in FIG. 9, the synchronous stimulation pulses and asynchronous stimulation pulses are used in combination for the stimulation during the mode transition period. In addition, when the mode is switched from the third stimulation mode to the fourth stimulation mode, as shown in FIG. 10, the stimulation pulses having an intermediate frequency between the high-frequency stimulation pulse and the low-frequency stimulation pulse are applied during the mode transition period.

By doing so, during the mode transition period, the heart A and the vagus nerve B can become accustomed to the stimulation mode after switching, thereby reducing the load exerted on the heart A and the vagus nerve B due to the switching of the stimulation mode.

In addition, in this embodiment, the controller 73 may control the voltage, pulse duration, pulse period, and duration of the stimulation pulses in the respective stimulation modes in accordance with the heartbeat detected by the heartbeat detection unit 4 or/and the cardiac dilatation level L calculated by the cardiac-dilatation-level calculating unit 71. For example, in the first and the second stimulation modes (synchronous modes), the voltage, pulse duration, and duration of the stimulation pulses may be increased in proportion to the heart rate R. In addition, in the first and the third stimulation modes (high-frequency modes), the pulse period of the stimulation pulses may be shortened in inverse proportion to the cardiac dilatation level L, or the voltage and pulse duration of the stimulation pulses may be increased in proportion to the cardiac dilatation level L.

As described above, by increasing the voltage and pulse duration of the stimulation pulses, or by reducing the pulse period of the stimulation pulses, the amount of energy possessed by the stimulation pulses is increased. Therefore, it is possible to further improve the therapeutic effect for an increased heart rate R and progressive cardiac dilatation.

In addition, in this embodiment, the organ-status detection unit that is illustrated with the impedance measuring unit 5 is provided in the main unit 2. Instead of this, a configuration in which an external apparatus (organ-status detection unit) that determines the organ status or the in-vivo information indicating the organ status is provided outside the body, and the data related to the organ status or the in-vivo information is acquired by the main unit 2 of the nerve stimulation apparatus 1 from the external apparatus through the communication unit (the in-vivo information acquisition unit) 9 is also possible.

Figure 11:
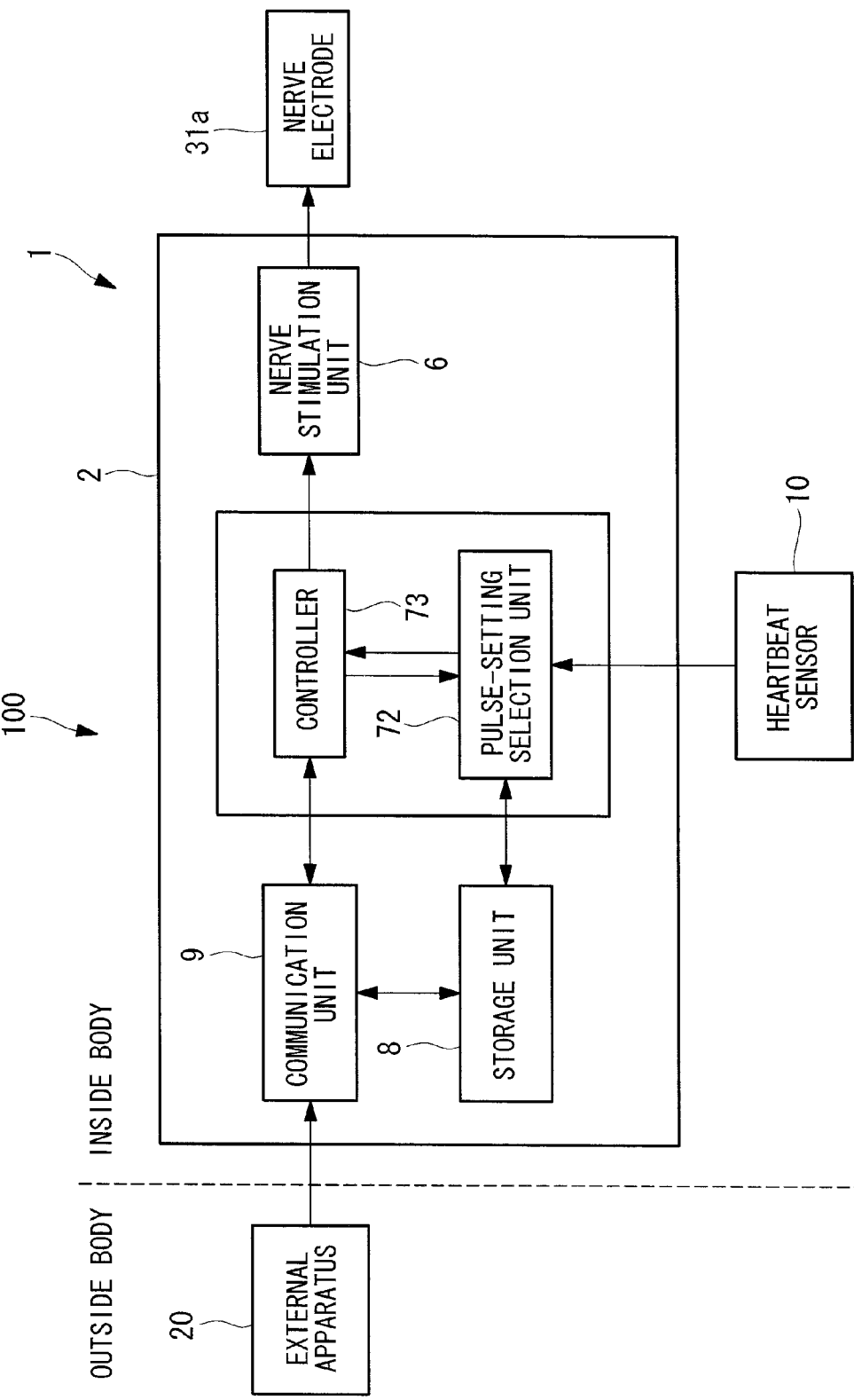
FIG. 11 is a block diagram showing the configuration of a nerve stimulation system according to an embodiment of the present invention.

FIG. 11 is a block diagram showing an example of the configuration of a nerve stimulation system 100 including an external apparatus 20. In FIG. 11, an example in which a heartbeat sensor 10 arranged outside the main unit 2 is used as the functional-status detection unit is shown. With such a configuration, the leads 32, 33, and 34 need not be inserted into the heart A, and it is possible to reduce the burden on the patient in whom the nerve stimulation apparatus 1 is implanted.

When an ultrasound observation device, an X-ray observation device, or an MRI observation device is used as the external apparatus 20, it is possible to measure the diameter of the heart A to be measured or the thickness of cardiac muscle from an image of the heart A as indicators of hypercardia, cardiac dilatation, or dilated cardiomyopathy. When a hemanalysis device is used as the external apparatus 20, it is possible to determine the amount of inflammatory marker in blood as an indicator of cardiac infarction. When an endoscope is used as the external apparatus 20, it is possible to diagnose the presence of or the degree of cardiac infarction from an endoscope image. When a thoracic impedance measuring device is used as the external apparatus 20, it is possible to determine the pulmonary impedance as an indicator of pulmonary congestion.

What is claimed is:

1. A nerve stimulation apparatus comprising:
    a heartbeat detection unit that detects a heartbeat;
    a nerve electrode that is connected to a nerve controlling a heart;
    a nerve stimulation unit that outputs an electrical pulse to the nerve electrode;
    a functional-status detection unit that detects in-vivo information that indicates a functional status of the heart;
    a stimulation-timing controller that controls the nerve stimulation unit so as to switch between a synchronous mode in which the electrical pulse is output in synchronization with the heartbeat detected by the heartbeat detection unit and an asynchronous mode in which the electrical pulses are output at constant time intervals, on the basis of the in-vivo information that indicates the functional status of the heart detected by the functional-status detection unit;
    an organ-status detection unit that detects in-vivo information that indicates the organ status of the heart; and
    a stimulation-frequency controller that controls the nerve stimulation unit so as to switch between a high frequency mode in which a plurality of the electrical pulses are output and a low-frequency mode in which the electrical pulses are output at a frequency lower than that in the high frequency mode, on the basis of the in-vivo information that indicates the organ status of the heart detected by the organ-status detection unit.

2. A nerve stimulation apparatus according to claim 1, wherein when the synchronous mode and the asynchronous mode are switched, the stimulation-timing controller has a mode transition period during which the nerve stimulation unit is controlled in both the synchronous mode and the asynchronous mode.

3. A nerve stimulation apparatus according to claim 1, wherein, in the synchronous mode, the nerve stimulation unit increase the amount of energy of the stimulation pulse in proportion to the in-vivo information that indicates the functional status of the heart.

4. A nerve stimulation apparatus according to claim 1, wherein the functional-status detection unit detects a heart rate, a blood pressure, a blood flow rate, or a left ventricular impedance.

5. A nerve stimulation apparatus according to claim 1, wherein the organ-status detection unit detects a left ventricular impedance, a pulmonary impedance, a cardiac contractile stress, an ST elevation in an electrocardiac signal, a QRS duration in an electrocardiac signal, or a level of dyssynchrony between both ventricles.

6. A nerve stimulation system comprising:
    stimulation apparatus according to claim 1 that is indwelled in body; and
    an external apparatus that is arranged outside body and that detects in-vivo information that indicates the organ status or the organ status of the heart;
    wherein the nerve stimulation apparatus is equipped with an in-vivo information acquisition unit that acquires the in-vivo information detected by the external apparatus; and
    a stimulation-frequency controller that controls the nerve stimulation unit so as to switch between a high-frequency mode in which a plurality of the electrical pulses are output and a low-frequency mode in which the electrical pulses are output at a frequency lower than that in the high-frequency mode, on the basis of the in-vivo information acquired by the in-vivo information acquisition unit.

7. A nerve stimulation system according to claim 6, wherein the external apparatus is an ultrasound observation device, an X-ray observation device, a nuclear magnetic resonance imaging device, a thoracic impedance measuring device, a hemanalysis device, or an endoscope.

8. A control method for a nerve stimulation apparatus for controlling a setting of an electrical pulse output from a pulse generator to an electrode with a controller provided in a nerve stimulation apparatus, wherein the controller controls the pulse generator so as to switch between a synchronous mode in which the electrical pulses are output in synchronization with a heartbeat and an asynchronous mode in which the electrical pulses are output at constant time intervals, on the basis of in-vivo information that indicates the functional status of the heart detected by a functional-status detection unit, and the controller controls the pulse generator so as to switch between a high-frequency mode in which a plurality of the electrical pulses are output and a low-frequency mode in which the electrical pulses are output at a frequency lower than that in the high-frequency mode, on the basis of in-vivo information that indicates the organ status of the heart, detected by an organ-status detection unit.

9. A control method for a nerve stimulation apparatus according to claim 8, wherein the controller controls the pulse generator such that, upon switching between the synchronous mode and the asynchronous mode, during a mode transition period between these two modes, the electrical pulses are output by superimposing the electrical pulses synchronous to the heartbeat in the synchronous mode and the electrical pulses at the constant time intervals in the asynchronous mode.

* * * * *